United States Patent [19]
McCool et al.

[11] Patent Number: 5,628,759
[45] Date of Patent: May 13, 1997

[54] FLEXIBLE SURGICAL RAZOR

[75] Inventors: Gregory F. McCool, Staunton; Jeffrey W. Wonderley, Fort Defiance, both of Va.

[73] Assignee: American Safety Razor Company, Verona, Va.

[21] Appl. No.: 313,597

[22] Filed: Sep. 29, 1994

[51] Int. Cl.$^6$ ........................................ A61B 17/32
[52] U.S. Cl. ........................ 606/167; 30/32; 30/346.5
[58] Field of Search ............................. 606/131, 132, 606/167; 30/32, 47, 48, 49, 50, 353, 346.5, 346.55, 346.61

[56] References Cited

U.S. PATENT DOCUMENTS

| | | | |
|---|---|---|---|
| 951,456 | 3/1910 | Saxton | 30/49 |
| 1,174,932 | 3/1916 | Grenier . | |
| 1,893,524 | 1/1933 | Shanley . | |
| 1,934,151 | 11/1933 | Slama et al. . | |
| 1,974,568 | 9/1934 | Grotenhuis . | |
| 2,035,110 | 3/1936 | Becker et al. . | |
| 2,041,778 | 5/1936 | Peters . | |
| 2,361,921 | 11/1944 | Albert | 30/50 |
| 2,453,198 | 11/1948 | Corbett | 30/312 |
| 3,583,403 | 6/1971 | Pohl et al. . | |
| 3,688,407 | 9/1972 | Paquette . | |
| 3,916,418 | 10/1975 | Neveu . | |
| 4,038,986 | 8/1977 | Mahler . | |
| 4,221,222 | 9/1980 | Detsch . | |
| 4,438,767 | 3/1984 | Nelson . | |
| 4,516,320 | 5/1985 | Peleckis | 30/49 |
| 4,651,734 | 3/1987 | Doss et al. . | |
| 4,690,139 | 9/1987 | Rosenberg . | |
| 4,782,590 | 11/1988 | Pope | 30/50 |
| 4,887,356 | 12/1989 | Rudd, Sr. . | |
| 4,893,641 | 1/1990 | Strickland . | |
| 4,943,295 | 7/1990 | Hartlaub | 606/131 |

OTHER PUBLICATIONS

DermQuest—"Introducing A Revolutionary New Biopsy Shaver" Brochure, Tampa, Florida (Jul. 1994).

*Primary Examiner*—Michael Powell Buiz
*Assistant Examiner*—Patrick W. Rasche
*Attorney, Agent, or Firm*—McDermott, Will & Emery

[57] ABSTRACT

A flexible surgical razor for removing organic tissue, such as lesions, moles, corns and the like, at or below the skin's surface. The surgical razor utilizes a flexible blade with a well-honed front edge and left and right gripping extensions formed attached to the left and right side edges of the blade, respectively. Each gripping extension includes an inner segment extending in the same plane as the blade, a middle segment extending at an upward angle away from the plane of the blade, and an exterior segment, with exterior gripping edges, extending at an intersecting angle with the middle segment. The front and rear edges of the gripping extensions run parallel to the front and rear edges of the blade. A flexible sheath is added to regulate the shape and extent of the blade's curvature. The user applies inward finger pressure to both gripping extensions simultaneously which bends the flexible blade in a curved fashion.

26 Claims, 5 Drawing Sheets

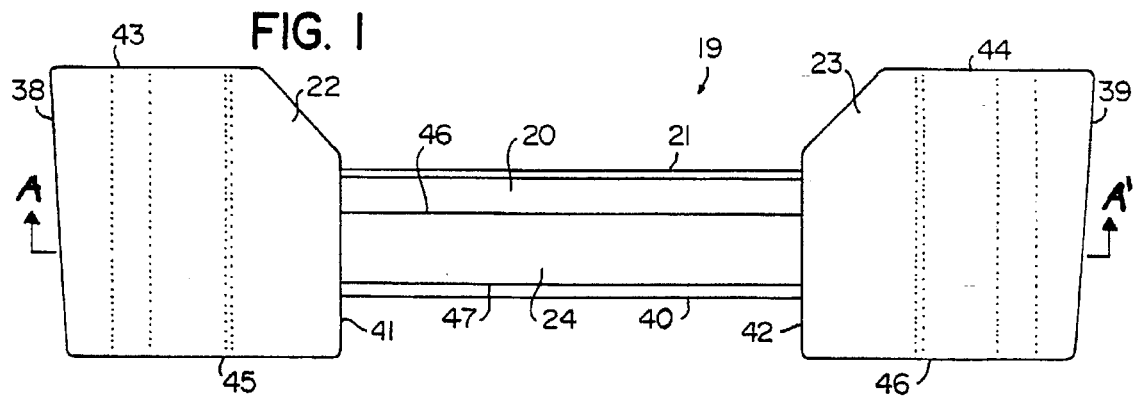
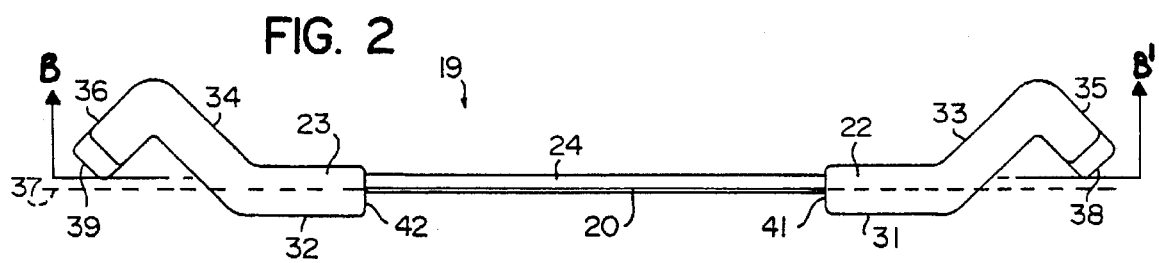
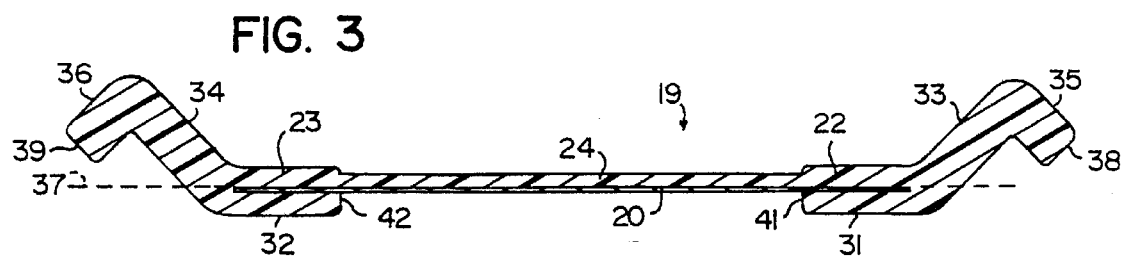
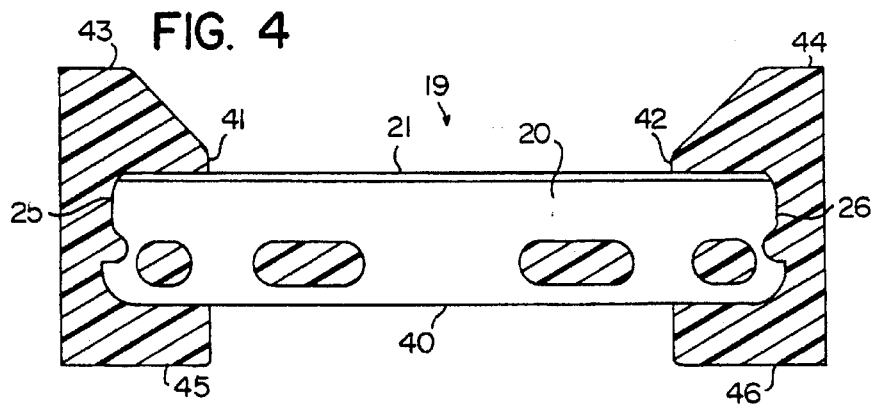

FLEXIBLE SURGICAL RAZOR

BACKGROUND OF THE INVENTION

The present invention is directed to an improved surgical instrument for cutting organic tissue at or below the skin's surface by employing a flexible blade with specially designed gripping extensions at both ends.

Medical professionals often remove organic tissue, such as lesions, moles, corns and the like, from the surface of a patients skin. Surgeons typically utilize a scalpel for such procedures, cutting around the appropriate area and to the desired depth. Removal of the organic tissue, however, also requires cutting underneath the unwanted tissue, and the scalpel is an awkward an inefficient tool for making such incisions. The straight and rigid scalpel blade requires angular cuts toward the center of the tissue to be removed, which results in the removal of more tissue than necessary. Consequently, many medical professionals have sought more efficient methods for performing such procedures.

Doctors utilize various instruments for cutting thin organic tissue sections for transplanting or grafting, such as U.S. Pat. Nos. 4,038,986 and 3,583,403. These instruments, however, are not designed for the removal of skin protuberances extending from below the skins surface. Such grafting devices shave large thin tissue sections of a preset width and thickness, and achieve smooth continuous cuts. Removal of small sections corresponding to lesions, moles, corns and the like ideally requires a thin flexible and readily adjustable blade for cutting small sections at varying depths. One particular flexible surgical cutting tool, U.S. Pat. No. 4,943,295, designed for the removal of skin protuberances, utilizes a thin flexible blade with finger grips and a sheath covering the rear margin of the blade. The surgeon applies pressure to the finger grips and bends the device to a desired degree of curvature depending on the width and depth of the intended incision. This invention, however, lacks a finger grip design for regulating the blade's flex. Moreover, this invention lacks a sheath design for controlling the shape and extent of the blade's curvature during use.

The present invention combines a flexible blade with gripping extensions designed to regulate the direction of the blade's flex and improve the surgeon's control over the extent of the blade's flex. Furthermore, the present invention teaches a method of varying the flexible sheath design for control over the shape and extent of the flexible blade's curvature.

SUMMARY OF THE INVENTION

The present invention provides a razor for removal of organic tissue, such as lesions, moles, corns and the like, at or below the skin's surface. The razor incorporates a flexible blade and a pair of gripping extensions. The flexible blade includes a well-honed front edge, a left side edge, a right side edge, a front edge, and a rear edge. The pair of gripping extensions are attached to the side edges of the flexible blade. The flexible blade may be bent to an appropriate curved cutting shape through the application of inward finger pressure on both gripping extensions simultaneously, while grasping the razor between the finger-tips.

Each gripping extension includes an inner, a middle and an outer segment. The inner segment is attached to a blade side edge and extends outward from the blade. The middle segment is extends at an upward angle away from the plane of the blade. The outer segment has an exterior gripping edge and extends at an intersecting angle with the middle segment. The points where the finger pressure is applied are thus above the plane of the flexible blade, a configuration which regulates the direction of the flexible blade's curvature and enhances the use's ability to control the extent of that curvature.

The invention may further include a flexible sheath that runs along the top surface of the flexible blade, and is attached to the gripping extensions. The front and rear edges of the flexible sheath are set inward from the front and rear edges of the flexible blade, respectively. Furthermore, the thickness, width and shape of the sheath control the flexibility of the razor. This flexibility regulates the user's control over the extent and shape of the flexible blade's curvature.

As pointed out in greater detail below, the razor of this invention provides important improvements and advantages over the existing art. The design of the gripping extensions facilitates efficient control over the direction and extent of the flexible blade's curvature during use. The design of the flexible sheath further enhances this control and also regulates the shape of the flexible blade's curvature. These advantages and improvements provide for a more versatile and effective razor.

The invention itself, taken together with further objects and attendant advantages, will best be understood by reference to the following detailed description taken in conjunction with the accompanying drawings.

BRIEF DESCRIPTION OF THE DRAWINGS

FIG. 1 is a top view of the flexible surgical razor of a first embodiment of this invention.

FIG. 2 is a front view of the flexible surgical razor of FIG. 1.

FIG. 3 is a cross section taken along line A-A' of FIG. 1.

FIG. 4 is a cross section taken along line B-B' of FIG. 2.

DETAILED DESCRIPTION

Figure 5:
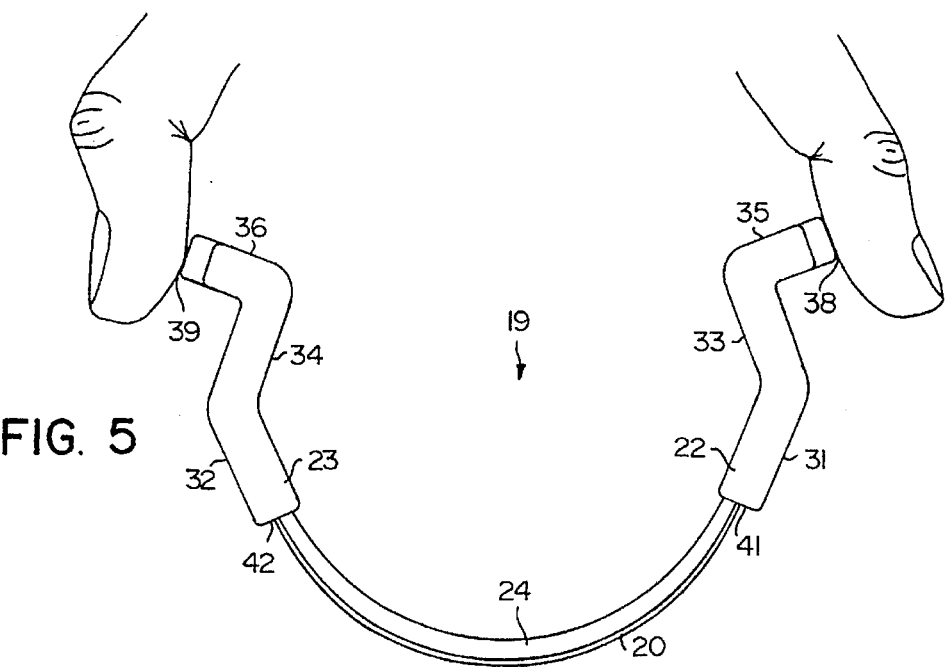
FIG. 5 is a front view of the flexible surgical razor of FIG. 1 in its flexed position as employed for the removal of organic skin tissue.

Turning to the drawings and a first embodiment of the invention, FIGS. 1-5 show a flexible surgical razor 19 for cutting organic skin tissue, such as lesions, moles, corns and the like, at or below the skin's surface. The flexible surgical razor 19 utilizes a thin, flexible blade 20 with a well-honed front edge 21, left and right gripping extensions 22 and 23, respectively, and a flexible sheath 24. As shown in FIG. 4, the flexible blade also includes left and right side edges 25 and 26, respectively.

FIGS. 2 and 3 illustrate the configuration of the left and right gripping extensions 22 and 23. The left and right inner segments 31 and 32 are attached to the flexible blade's left and right side edges 25 and 26, respectively, and extend outward from the flexible blade 20 with the left and right interior edges 41 and 42 facing inward towards the flexible blade 20. The right and left middle segments 33 and 34 extend outward from the left and right inner segments 31 and 32, respectively, and at upward angles away from the plane of the blade 37. The left and right outer segments 35 and 36, have exterior edges 38 and 39 for gripping, and extend outward from the middle segments 33 and 34, respectively, at intersecting angles with the left and right middle segments 33 and 34. The left and right front edges 43 and 44 of the left and right gripping extensions 22 and 23, respectively, run parallel to the front edge 21 of the flexible blade 20, and the left and right rear edges 45 and 46 of the left and right gripping extensions 22 and 23, respectively, run parallel to the rear edge 40 of the flexible blade 20.

The points where the inward finger pressure is applied to the left and right exterior edges 38 and 39 of the left and right gripping extensions 22 and 23 are thus above the plane of the blade 37. This configuration regulates the direction of the blade's curvature because the inward forces act above the plane of the blade 37 and thus create a resultant downward force on the flexible blade 20. Moreover, the gripping extension design enhances the user's ability to control the extent of the flexible blade's curvature through more efficient translation of the forces applied by the finger pressure.

The flexible sheath 24 runs across the top surface of the flexible blade 20, and attaches to the left and right interior edges 41 and 42 of the left and right gripping extensions 22 and 23, as depicted in FIGS. 1, 2 and 3. The front and rear edges 46 and 47 of the flexible sheath 24 are set inward from the front and rear edges 21 and 40 of the flexible blade 20, respectively. The thickness, width and shape of the flexible sheath 24 control the flexibility of the flexible surgical razor 19. Decreases in the thickness and/or width of the flexible sheath 24 will result in greater blade flexibility at the corresponding blade areas. The flexible blade's degree of curvature, therefore, will increase at the areas where the flexible sheath's thickness and/or width decreases.

The flexibility of this surgical razor enables the user to flex the instrument to an appropriate degree of curvature depending on the size and depth of the desired cut. The user curves the flexible blade 20 by applying inward pressure on the left and right exterior edges 38 and 39 of the left and right gripping extensions 22 and 23 simultaneously, while grasping the instrument between the finger-tips, as depicted in FIG. 5. The user controls the degree of curvature through the magnitude of the applied pressure. The flexible sheath 24 regulates the degree and shape of the flexible blade's curvature in accordance with the sheath's flexibility. Accordingly, the sheath's flexibility regulates the user's control over the extent and shape of the blade's curvature, as exhibited by the third and fourth embodiments described below.

Figure 6:
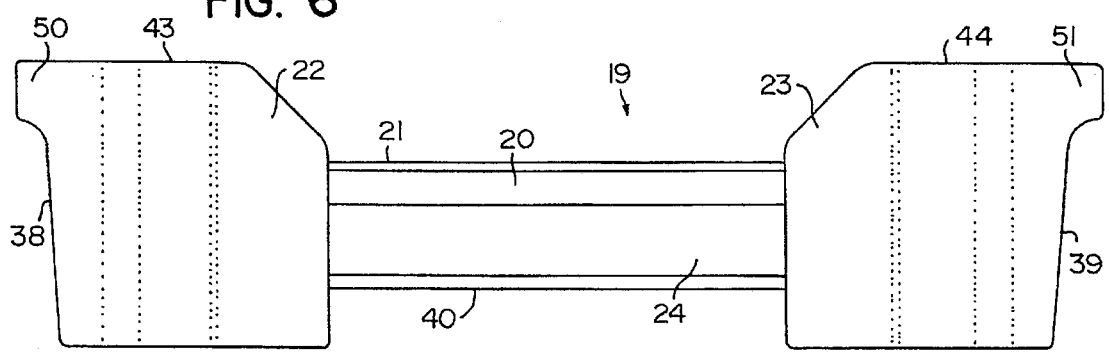
FIG. 6 is a top view of the flexible surgical razor of a second embodiment of this invention.
Figure 7:
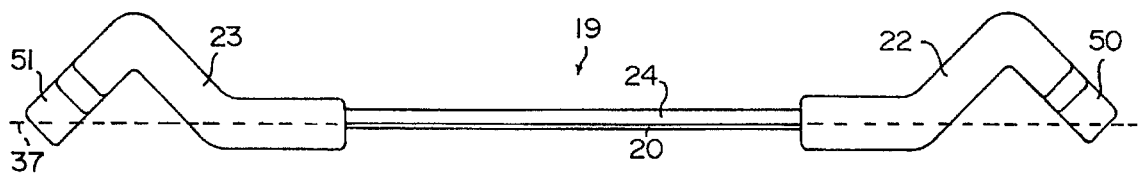
FIG. 7 is a front view of the flexible surgical razor of FIG. 6.

FIGS. 6 and 7 illustrate a second embodiment of the flexible surgical razor 19. This embodiment is identical to the first embodiment, described above, except for the addition of left and right protruding tabs 50 and 51, extending from the left and right exterior edges 38 and 39 of the left and right gripping extensions 22 and 23, respectively. The left and right protruding tabs 50 and 51 run along the left and right front edges 43 and 44 of the left and right gripping extensions 22 and 23, respectively. The left and right protruding tabs 50 and 51 provide surfaces for the user to press his finger tips against while guiding the flexible blade across the surface of the patient's skin.

Figure 8:
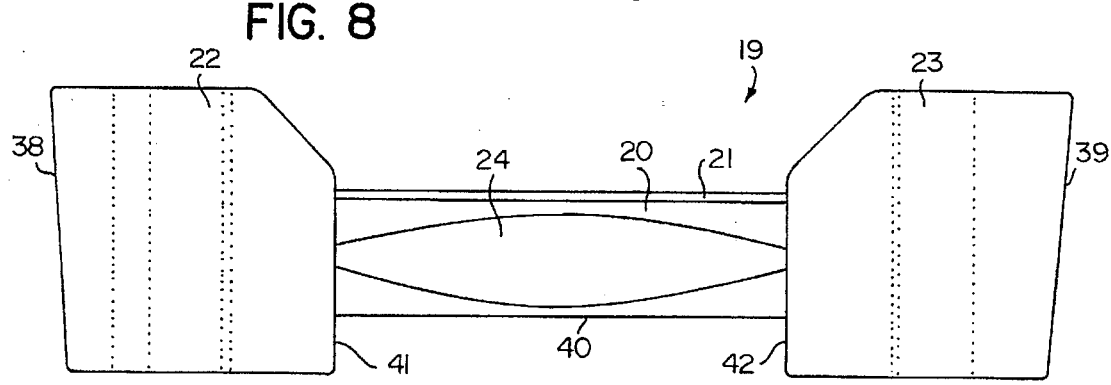
FIG. 8 is a top view of the flexible surgical razor of a third embodiment of this invention.
Figure 9:
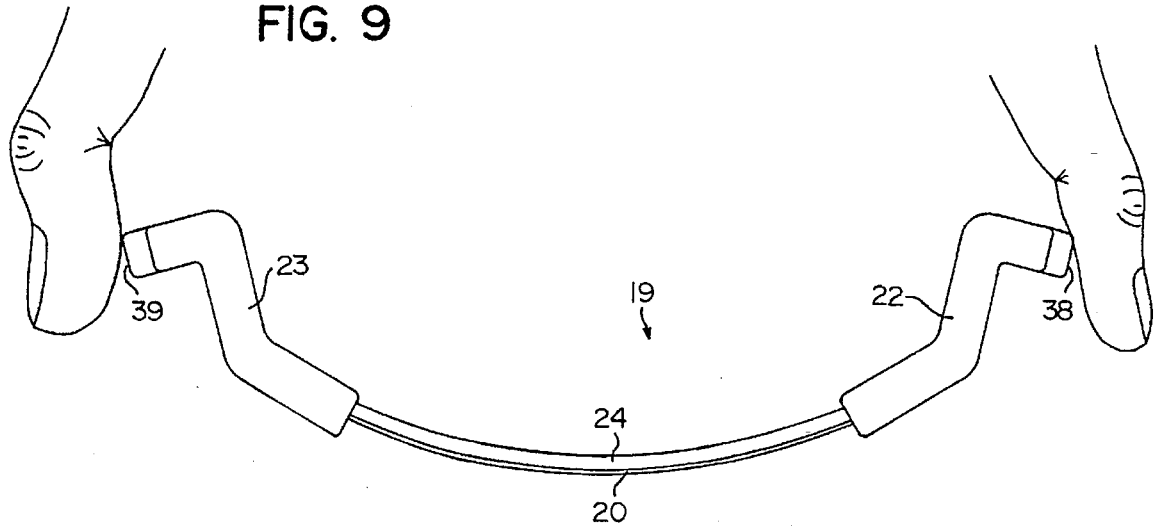
FIG. 9 is a front view of the flexible surgical razor of FIG. 8 in its flexed position as employed for the removal of organic skin tissue.
Figure 10:
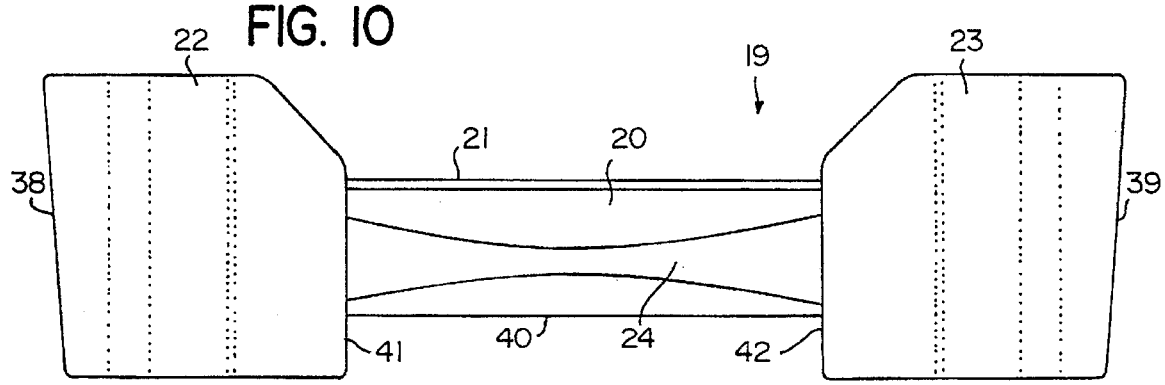
FIG. 10 is a top view of the flexible surgical razor of a fourth embodiment of the present invention.

A third embodiment of the flexible surgical razor 19, in FIGS. 9 and 10, illustrates a modified flexible sheath design. This embodiment is identical to the first embodiment, described above, except that the front and rear edges 46 and 47 of the flexible sheath 24 are designed with a convex shape, as illustrated in FIG. 8. This flexible sheath design will result in a flex as depicted in FIG. 9. The wider portion of the flexible sheath 24 will react less to inward finger pressure applied to the left and right exterior edges 38 and 39 of the left and right gripping extensions 22 and 23 than the narrower portions. This produces the lesser degree of curvature portrayed in FIG. 9.

Figure 11:
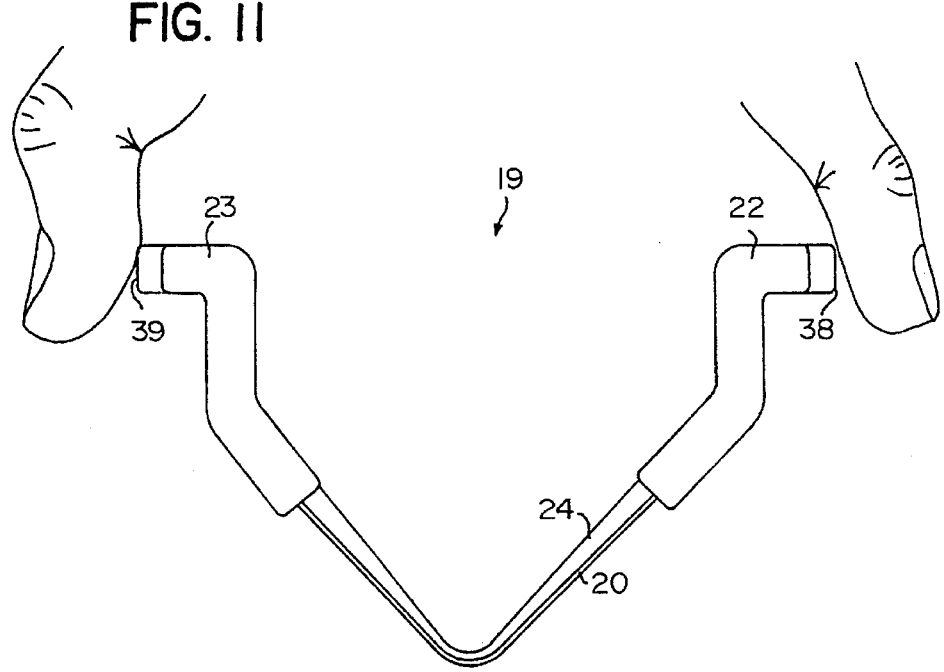
FIG. 11 is a front view of the flexible surgical razor of FIG. 10 in its flexed position as employed for the removal of organic skin tissue.

A fourth embodiment of the flexible surgical razor 19, in FIGS. 10 and 11, illustrates another alternative flexible sheath design. This embodiment is identical to the first embodiment, described above, except that the front and rear edges 46 and 47 of the flexible sheath 24 are designed with a concave shape, as illustrated in FIG. 10. This flexible sheath design will result in a flex as depicted in FIG. 11. The wider portions of the flexible sheath 24 will react less to inward finger pressure applied to the left and right exterior edges 38 and 39 of the left and right gripping extensions 22 and 23 than the narrower portions. This produces the sharp degree of curvature portrayed in FIG. 11.

Figure 12:
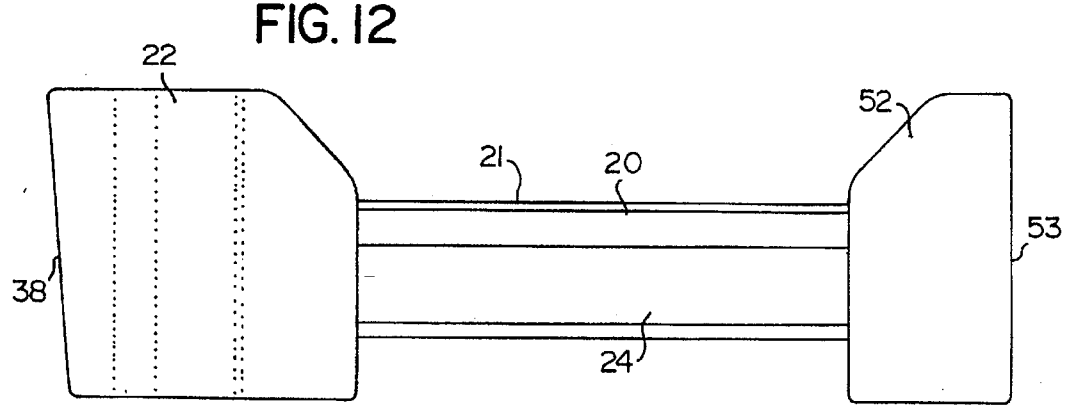
FIG. 12 is a top view of the flexible surgical razor of a fifth embodiment of the present invention.
Figure 13:
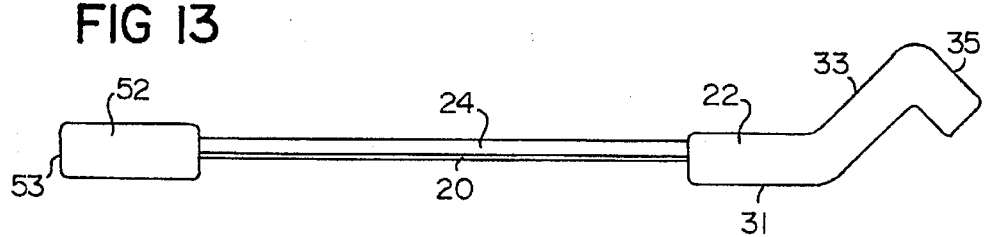
FIG. 13 is a front view of the flexible surgical razor of FIG. 12.

A fifth embodiment of the present invention only utilizes one specially designed gripping extension 22, as depicted in FIGS. 12 and 13. This embodiment is identical to the first embodiment, described above, except that only one of the gripping extensions 22 includes the inner 31, middle 33 and outer 35 segments, configured as described in the first embodiment. The other gripping extension only requires one segment 52, with an exterior gripping edge 53, attached to the other side edge of the flexible blade 20.

The embodiments described above provide for some significant improvements and advantages. A first advantage lies in the design of the left and right gripping extensions 22 and 23. As described above, the gripping extensions 22 and 23 regulate the direction of the flexible blade's curvature and improve the user's control over the extent of that curvature. Moreover, the design of the flexible sheath 24 facilitates further control over the extent of the flexible blade's curvature and regulates the flexible blade's shape. The third and fourth embodiments, described in detail above, depict the flexible sheath's effect on blade curvature, demonstrating the expanded versatility of this flexible surgical razor.

Of course, it should be understood that a wide range of changes and modifications can be made to the preferred embodiment described above. It is therefore intended that the foregoing detailed description be regarded as illustrative rather than limiting, and that it be understood that it is the following claims, including all equivalents, which are intended to define the scope of the invention.

We claim:

1. A razor comprising:

a flexible blade having a front edge, left and right side edges, and a rear edge; and a pair of gripping extensions each having a planar inner segment attached to a side edge of said blade, an at least partially planar middle segment extending at an upward angle away from the plane of the blade, and an outer segment having an exterior gripping edge and extending at an intersecting angle with said middle segment, said flexible blade flexing upon application of finger pressure to said gripping extensions.

2. The razor of claim 1 wherein said pair of gripping extensions further comprise a front edge running parallel to the front edge of the blade, and a rear edge running parallel to the rear edge of the blade.

3. The razor of claim 1 wherein said pair of gripping extensions mirror each other.

4. The razor of claim 1, further comprising a flexible sheath.

5. The razor of claim 4 wherein said flexible sheath is connected to said pair of gripping extensions.

6. The razor of claim 4 wherein said flexible sheath includes concave edges relative to both the front and rear edges of said flexible blade.

7. The razor of claim 4 wherein the thickness and the width of said sheath controls the flexing of said flexible blade in response to finger pressure applied to said gripping extensions.

8. The razor of claim 4 wherein said flexible sheath includes convex edges relative to both the front and rear edges of said flexible blade.

9. The razor of claim 1, wherein said exterior edges of said pair of gripping extensions are tapered at an inward angle toward the rear edge of said flexible blade.

10. The razor of claim 1, having protruding tabs extending from said exterior edges of said pair of gripping extensions.

11. A razor comprising:
   a flexible blade having a front edge, left and right side edges, and a rear edge;
   one gripping extension having a planar inner segment attached to a side edge of said blade, an at least partially planar middle segment extending at an upward angle away from the plane of the blade, and an outer segment having an exterior gripping edge and extending at an intersecting angle with said middle segment; and
   a gripping extension attached to the other side edge of said flexible blade and having an exterior gripping edge.

12. The razor of claim 11 wherein said pair of gripping extensions further comprise a front edge running parallel to the front edge of the blade, and a rear edge running parallel to the rear edge of the blade.

13. The razor of claim 11, further comprising a flexible sheath.

14. The razor of claim 13 wherein said flexible sheath is connected to said gripping extensions.

15. The razor of claim 13 wherein said flexible sheath includes concave edges relative to both the front and rear edges of said flexible blade.

16. The razor of claim 13 wherein the thickness and the width of said sheath controls the flexing of said flexible blade in response to finger pressure applied to said gripping extensions.

17. The razor of claim 13 wherein said flexible sheath includes convex edges relative to both the front and rear edges of said flexible blade.

18. The razor of claim 11, wherein said exterior edges of said pair of gripping extensions are tapered at an inward angle toward the rear edge of said flexible blade.

19. The razor of claim 11, having protruding tabs extending from said exterior edges of said gripping extensions.

20. A flexible surgical razor, comprising:
   a flexible blade having a well-honed front edge, left and right side edges, and a rear edge;
   a left gripping extension, including a planar left inner segment attached to the flexible blade's left side edge, an at least partially planar left middle segment extending at an upward angle away from the plane of the blade, and a left outer segment, with a left exterior gripping edge, extending at an intersecting angle with said left middle segment; and
   a right gripping extension, including a planar right inner segment attached to the flexible blade's right side edge, an at least partially planar right middle segment extending at an upward angle away from the plane of the blade, and a right outer segment, with a right exterior gripping edge, extending at an intersecting angle with said right middle segment, said flexible blade flexing upon application of finger pressure to said gripping extensions.

21. The flexible surgical razor of claim 20 wherein said left and right gripping extensions further comprise left and right front edges running parallel to the front edge of said flexible blade, and left and right rear edges running parallel to the rear edge of said flexible blade.

22. The flexible surgical razor of claim 20 further comprising, a flexible sheath running along the top surface of the blade and connected to the left and right interior edges of said left and right gripping extensions, wherein the thickness and width of said sheath controls the flexibility of said flexible blade.

23. The flexible surgical razor of claim 22 wherein said flexible sheath includes convex edges relative to both the front and rear edges of said flexible blade.

24. The flexible surgical razor of claim 20, wherein the left and right exterior edges of said left and right gripping extensions are tapered at an inward angle toward the rear edge of said flexible blade.

25. The flexible surgical razor of claim 20, wherein left and right protruding tabs extend from the left and right exterior edges of said left and right gripping extensions, respectively.

26. The flexible surgical razor of claim 22 wherein said flexible sheath includes concave edges relative to both the front and rear edges of said flexible blade.

* * * * *